United States Patent
Geyer et al.

(10) Patent No.: US 7,159,824 B2
(45) Date of Patent: Jan. 9, 2007

(54) DEVICE AND METHOD FOR ON-ORBIT CALIBRATION VERIFICATION OF AN INFRARED SENSOR

(75) Inventors: David W. Geyer, Santa Barbara, CA (US); Russell Shea Ferring, Titusville, FL (US); Richard D. Nielsen, Merritt Island, FL (US)

(73) Assignee: Analex Corporation, Alexandria, VA (US)

( * ) Notice: Subject to any disclaimer, the term of this patent is extended or adjusted under 35 U.S.C. 154(b) by 154 days.

(21) Appl. No.: 10/654,454

(22) Filed: Sep. 4, 2003

(65) Prior Publication Data

US 2005/0051670 A1     Mar. 10, 2005

(51) Int. Cl.
*B64G 1/00* (2006.01)

(52) U.S. Cl. .............................. 244/158.1; 244/171.7; 250/252.1; 250/341.5

(58) Field of Classification Search ............. 244/158.1, 244/171.7; 250/252.1, 339.09, 341.5
See application file for complete search history.

(56) References Cited

U.S. PATENT DOCUMENTS

| | | | |
|---|---|---|---|
| 4,527,619 A | * | 7/1985 | Cartier et al. .................. 165/41 |
| 5,602,389 A | * | 2/1997 | Kato et al. ................ 250/252.1 |
| 5,716,030 A | | 2/1998 | LaFiandra et al. ...... 244/158 R |
| 6,027,076 A | * | 2/2000 | Krause .................... 244/158 R |
| 6,294,785 B1 | * | 9/2001 | Gordley ................. 250/339.09 |

OTHER PUBLICATIONS

John J. Degnan, "SLR2000 Project: Engineering Overview and Status," NASA Goddard Space Flight Center, pp. 389-398.

* cited by examiner

*Primary Examiner*—J. Woodrow Eldred
(74) *Attorney, Agent, or Firm*—Finnegan, Henderson, Farabow, Garrett & Dunner, L.L.P.

(57) ABSTRACT

A device for verifying the calibration of an infrared sensor includes a body configured to be placed in orbit. The body defines a spin axis and an outer surface. The outer surface has an infrared radiant intensity that is substantially independent of the viewing angle between the spin axis of the body and the infrared sensor. The device may be used for on-orbit verification of the calibration coefficients associated with each pixel of an infrared sensor, including linearity calibration and verification of the resolution capability of the sensor. The calibration coefficients may be verified over the entire sensing capability range of the infrared sensor. After a thermal model of the device is developed, the device operates passively and provides a known source of infrared radiation observable during the device's entire orbital lifetime. The device may be designed to automatically de-orbit from space after a predictable time in orbit.

42 Claims, 3 Drawing Sheets

DEVICE AND METHOD FOR ON-ORBIT CALIBRATION VERIFICATION OF AN INFRARED SENSOR

BACKGROUND OF THE INVENTION

1. Field of the Invention

The present invention relates to a device for verifying the calibration of sensors and, more particularly, to an orbiting device for verifying the calibration of infrared sensors.

2. Description of the Related Art

Infrared sensors are designed to detect and measure thermal radiation emanating from remote objects. In order to accurately determine the infrared characteristics of remote objects, the values of the calibration coefficients used with an infrared sensor must be developed. Developing the values of such coefficients involves exposing the sensor to primary reference standards having precisely known infrared characteristics at known frequencies, measuring the sensor's output, and developing coefficients such that the compensated sensor output is as close as possible to the value of the primary source.

The accuracy of the calibration coefficients associated with the sensor may be subsequently verified by measuring the sensor's output when it is exposed to secondary reference standards having infrared characteristics that are known with less precision. The term "infrared sensor" as used herein includes the object on which the infrared energy is focused (e.g., focal plane array or scanning array), the associated electronics that create a digital output from the array's analog output, and the software used to transform the relative output of the pixels in the sensor, on a pixel by pixel basis, into a common absolute reference by applying one or more calibration coefficients to the measured output of each pixel.

In one example, a space-based infrared sensor is calibrated on the ground using one or more known temperature sources (primary reference standards). The accuracy of the coefficients used to calibrate the sensor, as well as the stability of the sensor and associated electronics, are subsequently verified on-orbit by having the sensor view a star with a known radiant intensity and temperature (a secondary reference standard), and measuring the compensated sensor's output against the known value of the star's radiant intensity.

As used herein, "verifying the calibration of an infrared sensor" means comparing the compensated output of a sensor that is viewing an object having a known infrared intensity at frequency bands of interest, to the object's known infrared intensity at the same frequency bands, and determining whether or not the sensor system is operating correctly and within specification, and/or potentially updating the calibration coefficients used with the sensor system to reduce any observed errors in the compensated output of the sensor.

Both active and passive devices have been used as secondary reference standards. Active devices use powered energy sources, such as electrical heaters, to heat a radiant surface to a desired reference temperature. Temperature sensors are used to ensure that the radiant surface is maintained at the reference temperature Passive devices are heated by ambient temperatures and external radiant energy sources, such as the sun. These devices are provided with surface coatings having a selected absorptivity and emissivity to maintain the radiant surface at a desired reference temperature. Such passive devices are typically designed to act as black body sources, i.e., sources that emit radiation that is entirely dependent upon their temperatures.

Conventional devices have several drawbacks. For example, U.S. Pat. No. 5,716,030 discloses a spacecraft telescope door having a panel for providing a radiant temperature reference for verifying a calibration of an infrared sensor. The panel is coated with a highly emissive paint having a low reflectance. The panel is also provided with electrical heaters and temperature sensors to allow either active or passive operation.

One drawback of this device is that the telescope door must be closed when the panel is in use. In addition, where active mode operation is required, the useful life of the device is limited by the longevity of its power supply.

A further drawback of this device is the limited dynamic range over which the calibration can be verified using the device. For example, when the telescope door closes and the panel is presented to the infrared sensor, all of the pixels of the sensor are exposed to the panel at the same time and at the same temperature, as the image of the door is not in focus on the focal plane array.

SUMMARY OF EXEMPLARY ASPECTS

In the following description, certain aspects and embodiments of the present invention will become evident. It should be understood that the invention, in its broadest sense, could be practiced without having one or more features of these aspects and embodiments. It should also be understood that these aspects and embodiments are merely exemplary.

One aspect relates to a device for verifying the calibration of an infrared sensor. The device may comprise a body configured to be placed in orbit, the body defining an outer surface and a spin axis. The outer surface may have an infrared radiant intensity that is substantially independent of a viewing angle between the spin axis of the body and the infrared sensor, significantly reducing the task of determining the value of the radiant intensity that should be present at the location of the remote infrared sensor being calibrated.

As used herein, "orbit," "orbiting," and "on-orbit" broadly encompass suborbital and orbital trajectories having altitudes of approximately 100,000 feet and higher.

In another aspect, the device may further comprise at least one locator element disposed on the body. The at least one locator element may comprise a reflector for a laser. In some embodiments, the at least one locator element may comprise a plurality of locator elements. The configuration of the at least one locator element is chosen so as to minimize the radiant intensity variation of the body versus the viewing angle of the body. Consideration is also given to the location of the locator element with respect to the viewing angle.

In some embodiments, the device may further comprise at least one sensor associated with the body and a power supply. The at least one sensor may comprise a temperature sensor or a plurality of temperature sensors.

In some embodiments, the device may further comprise a transmitter for transmitting data obtained by the at least one sensor. The device may further comprise a data storage device for storing data obtained by the at least one sensor. In one aspect, the transmitter may transmit data from the data storage device.

In some embodiments, the device may further comprise a receiver for receiving control signals. In one aspect, the transmitter may transmit data in response to a control signal received by the receiver.

In some embodiments, the device may further comprise a monopole antenna utilized by the transmitter in transmitting data and by the receiver in receiving data. The location and type of monopole antenna are selected to reduce the variation in radiant intensity of the body when viewed at any aspect angle with respect to the spin axis of the body.

According to a further aspect, the outer surface may have an infrared radiant intensity that is substantially independent of operation of the transmitter and the receiver.

Another aspect relates to a device for verifying the calibration of an infrared sensor that may comprise a body configured to be placed in orbit, the body defining an outer surface and a spin axis. The outer surface may have an infrared radiant intensity that is substantially independent of any internal heat sources.

In some embodiments, the device may further comprise at least one thermal sensor disposed on the body, a transmitter for transmitting data obtained by the at least one thermal sensor, and a receiver for receiving control signals. The transmitter may transmit data in response to a control signal received by the receiver.

In some embodiments, the device may further comprise a power supply and at least one locator element disposed on the body. The at least one locator element may be configured to allow the device to be tracked by an external tracking device.

A still further aspect relates to a method of verifying the calibration coefficients used with a plurality of pixels associated with an infrared sensor. The method may comprise providing a body defining an outer surface and a spin axis, wherein the outer surface has an infrared radiant intensity that is substantially independent of a viewing angle between the spin axis and the infrared sensor. The method may further comprise placing the body in orbit, measuring the infrared radiant intensity of the outer surface using a first group of one or more pixels associated with the infrared sensor to obtain a first measurement, and measuring the infrared radiant intensity of the outer surface using a second group of one or more pixels associated with the infrared sensor to obtain a second measurement.

The term "providing" is used in a broad sense, and refers to, but is not limited to, making available for use, enabling usage, giving, supplying, obtaining, getting a hold of, acquiring, purchasing, selling, distributing, possessing, making ready for use, and/or placing in a position ready for use.

According to another aspect, a method of verifying the calibration of an infrared sensor at various observed energy levels may comprise providing a body defining an outer surface and a spin axis, wherein the outer surface has an infrared radiant intensity that is substantially independent of a viewing angle between the spin axis and the infrared sensor. The method may further comprise placing the body in orbit, measuring the infrared radiant intensity of the outer surface using the infrared sensor when the body and the infrared sensor are in a first geometrical relationship to obtain a first measurement, and measuring the infrared radiant intensity of the outer surface using the infrared sensor when the body and the infrared sensor are in a second geometrical relationship to obtain a second measurement.

In some embodiments, in the first geometrical relationship the body and the infrared sensor may be spaced at a first distance, and in the second geometrical relationship the body and the infrared sensor may be spaced at a second distance greater than the first distance.

A further aspect relates to a method of verifying a resolution capability of an infrared sensor. The method may comprise providing a plurality of bodies, each body defining an outer surface and a spin axis, wherein the outer surface has an infrared radiant intensity that is substantially independent of a viewing angle between the spin axis and the infrared sensor. The method may further comprise placing the bodies in orbit proximate to each other with a known or predictable location with respect to each other, measuring the infrared radiant intensity of the outer surface of each body using the infrared sensor, and then determining whether or not the calculated values of the positions of the bodies as determined by the sensor are commensurate with the known positions of the bodies.

In some embodiments, the method may further comprise differentiating between the bodies based on the infrared radiant intensity measurements associated with each body, where each body can be tailored to have a known, predictable value of radiant intensity versus infrared frequency band.

Yet another aspect relates to a method of using a calibration verification device comprising a body defining an outer surface and a spin axis, wherein the outer surface has an infrared radiant intensity that is substantially independent of a viewing angle between the spin axis and an infrared sensor. The method may comprise collecting thermal data from the body, transmitting the thermal data to a receiving station, and developing a thermal model of the body that allows determination of a predicted radiant intensity of the outer surface based on the collected thermal data.

In some embodiments, the method may further comprise measuring the radiant intensity of the outer surface over a frequency range of interest and comparing the measured radiant intensity with the predicted radiant intensity over the frequency range.

In some embodiments, the spin axis of the body is perpendicular to the plane of the ecliptic of the earth's orbit. This orientation minimizes the variations in the temperature and the associated radiant intensity of the outer surface induced by the radiation incident on the body from the sun as the body rotates about its spin axis. In other embodiments, the spin axis of the body is located at a known angle with respect to the plane of the ecliptic of the earth's orbit to deliberately induce regular variations in the radiated intensity from the body as the body rotates.

Aside from the structural and procedural arrangements set forth above, the invention could include a number of other arrangements such as those explained hereinafter. It is to be understood that both the foregoing description and the following description are exemplary only.

BRIEF DESCRIPTION OF THE DRAWINGS

The accompanying drawings, which are incorporated in and constitute a part of this specification, illustrate several exemplary embodiments of the invention and together with the description, serve to explain the principles of the invention. In the drawings.

DETAILED DESCRIPTION OF EXEMPLARY EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Figure 1:
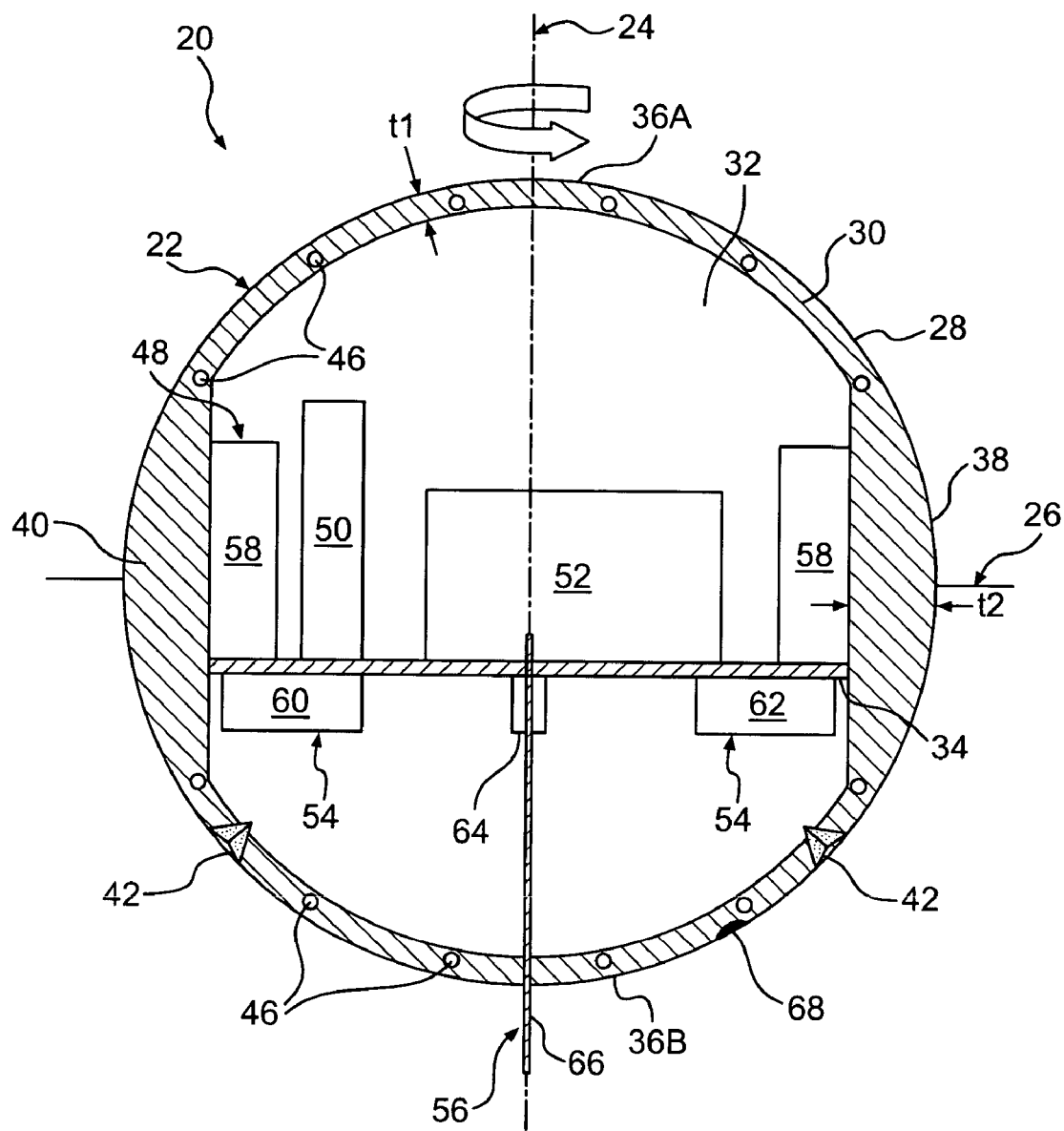
FIG. 1 is a schematic cross-sectional view of an embodiment of a device for verifying the calibration of an infrared sensor according to the present invention.

An embodiment of a device 20 for verifying the calibration of an infrared sensor is shown in FIG. 1. The device 20 comprises a body 22 configured to be placed in orbit. The body defines a spin axis 24, about which the body 22 rotates while in orbit, an ecliptic plane 26 substantially perpendicular to the spin axis 24, and an outer surface 28. The outer surface 28 has an infrared radiant intensity that is substantially independent of a viewing angle between the spin axis 24 of the body and the infrared sensor (not shown). In one example, one or more devices may be launched into a low earth orbit using a standard launch vehicle. The devices could have, for example, a mass of 30 to 50 kg. Devices having other masses could also be used. Depending upon mission requirements, the orbit of the device could have an altitude ranging from 500 to 650 km and an inclination ranging from 50 to 100 degrees. A sun-synchronous orbit may be adopted in order to provide a more consistent thermal environment.

The deployment of the device 20 from the launch vehicle is used to introduce a spin to the device 20 perpendicular to its ecliptic plane 26. This spin may both assist in stabilizing the device 20 and minimizing solar induced temperature variations.

The body 22 comprises a shell 30 defining an inner compartment 32. A platform 34 is disposed within the inner compartment 32 to support internal components of the device, as described below.

As shown in FIG. 1, the shell 30 has a substantially spherical shape. The maximum diameter of the shell 30 is limited only by the ability to launch the device 20 into orbit. Typically, the diameter ranges from approximately 20 to approximately 50 centimeters, but shells having larger or smaller diameters may also be used.

The shell 30 defines polar regions 36A, 36B at either end of the spin axis 24 and an equator region 38 near the ecliptic plane 26. In the vicinity of the polar regions 36A, 36B, the shell 30 has a first thickness t1. In the vicinity of the equator region 38, the shell 30 has a second thickness t2 that is thicker than the first thickness t1. Neither of these thicknesses t1, t2 need be constant. For example, mounting bosses in the polar regions 36A, 36B may result in local increases in thickness. Alternatively, the polar regions 36A, 36B may be designed to be thinner near the spin axis 24 and thicker farther from the spin axis 24.

As shown in FIG. 1, the thickness t2 is greatest at the ecliptic plane 26 and tapers down to the thickness t1 at a distance from the ecliptic plane 26. The thickness of the shell at the various locations is chosen so as to ensure the stability of the spin axis of the body during the orbital lifetime of the body, to minimize the temperature variation of the emitted radiation versus aspect angle of the body, and to provide a weight-to-frontal area of the body such that a reasonably predicted re-entry time of the body from orbit can be obtained.

The shell thickness t1 in the vicinity of polar regions 36A, 36B may be on the order of one to two centimeters. Such a relatively thick shell 30 may facilitate the equalization of the temperature distribution experienced by the shell 30.

The shell thickness t2 in the vicinity of the equator region 38 may be considerably thicker than the thickness t1. This concentrated mass girdle 40 near the ecliptic plane 26 establishes a first principal moment of inertia around the spin axis 24, thereby ensuring a preferred axis of rotation and a fixed spin axis over time. The location of the components within the body is also chosen so as to ensure the stability of the preferred axis of rotation of the body over the orbital lifetime of the body.

The girdle 40 need not be continuous or formed of the same material as the rest of the shell 30. For example, in the case of a shell 30 having a relatively constant thickness, the girdle 40 may be formed from a plurality of contiguous or non-contiguous plates secured to an inner surface of the shell 30 near the ecliptic plane 26 to establish a first principal moment of inertia around the spin axis 24. The spin axis 24 may be oriented such that the thermal stability of the body 22 can be maintained. Alternatively, a girdle 40 may be formed by strategically placing the internal components of the device 20 near the ecliptic plane 26 and as close to the shell 30 as possible.

The shell 30 may be made of one or more materials, of which at least one is a thermally conducting material. For example, the shell 30 may comprise at least one of aluminum, titanium, steel, copper, nickel, magnesium, and their alloys. Thermoelastic or thermoplastic composite materials, such as fiberglass, graphite, or KEVLAR-reinforced epoxies may also be used.

In some embodiments, the thicknesses t1, t2 of the shell 30 and its material, in conjunction with the diameter of the shell 30 and the weight of the internal components of the device 20, are chosen so that the cross-sectional area-to-mass ratio of the device 20 falls within a range of 0.002 to 0.007 meters$^2$/kilogram. This area-to-mass ratio may be further tailored, given a specific set of orbital parameters (e.g., altitude and inclination), to yield a select orbital lifetime for the device 20, for example, between 20 and 25 years. This feature provides a passive mechanism for ensuring a reliable orbital decay at a predictable time.

The outer surface 28 of the shell 30 may be partially or completely covered with one or more surface coatings. The coatings may include, for example, materials having low absorptivity and low emissivity (e.g., flat reflectors), materials having high absorptivity and high emissivity (e.g., flat absorbers), materials having high absorptivity and low emissivity (e.g., solar absorbers), and materials having low absorptivity and high emissivity (e.g., solar reflectors). For example, the surface absorptivity and high emissivity (e.g., solar reflectors). For example, the surface coating may include organic and/or inorganic materials, such as acrylic paints, silicone paints, and epoxies. In one embodiment, the outer surface 28 has an emissivity ranging from approximately 0.1 to approximately 1.0 over a radiant energy range of interest.

Depending upon the desired absorptivity or emissivity properties, the surface coating may include white paint, black paint, metallic paint, or any combination thereof. A single paint may cover substantially the entire outer surface 28 or two or more paints could be used. The surface coating may also include anodized layers or other electrolytically obtained coatings. In addition, the surface coating may include materials electrochemically or vapor deposited onto the outer surface 28 of the shell 30.

The features of the outer surface 28 also depend on the finish provided to the material. In one example, the outer surface of a stainless steel shell was sand-blasted to provide a surface having a relatively high absorptivity and high emissivity. In another example, the outer surface of an aluminum shell was polished to provide a surface having a relatively high absorptivity and low emissivity. A variety of other finishes may be provided to achieve a desired set of radiant properties.

Another consideration in selecting a surface coating is the issue of solar glint (i.e., reflection) from the outer surface 28 of the device 20 into the field of view of the infrared sensor for which the calibration is being verified.

Additional parameters to consider in selecting a surface coating include the emissivity and absorptivity of the surface coating, as well as the on-orbit stability of the emissivity and absorptivity of the coating by radiant frequency. In addition, when selecting a specific surface coating, consideration should be given to on-orbit degradation of the coating due to exposure to ultraviolet radiation, ionizing radiation, and/or atomic oxygen. Further considerations include possible degradation of the surface coating due to thermal cycling, meteoroid or other particulate matter impacting the coating, and/or contamination during the satellite manufacture and launch phases.

Typically, the surface coating is selected to provide a desired radiant intensity characteristic for a device of a given size. Varying the design parameters of the device 20, such as, for example, the diameter of the shell 30 and/or the surface coating, allows the radiant intensity of the outer surface 28 to be tailored to a desired range. Accordingly, the device 20 may be constructed to provide the outer surface 28 with a desired radiant intensity. In one embodiment, the outer surface 28 has an infrared radiant intensity ranging from approximately $10^{-1}$ Watts per steradian to approximately 10 Watts per steradian.

A wide range of radiant intensities emanating from the body are attainable due to the variety of design features that may be modified. The measured intensity is also dependent on the geometric relationship between the body and the infrared sensor at the time the measurements are taken. This geometric relationship can be widely variable by choice. Thus, bodies may be constructed having appropriate radiant intensities, as observed by the sensor, to allow the calibration of the pixels associated with an infrared sensor over their full range of measurement sensitivity.

Figure 2:
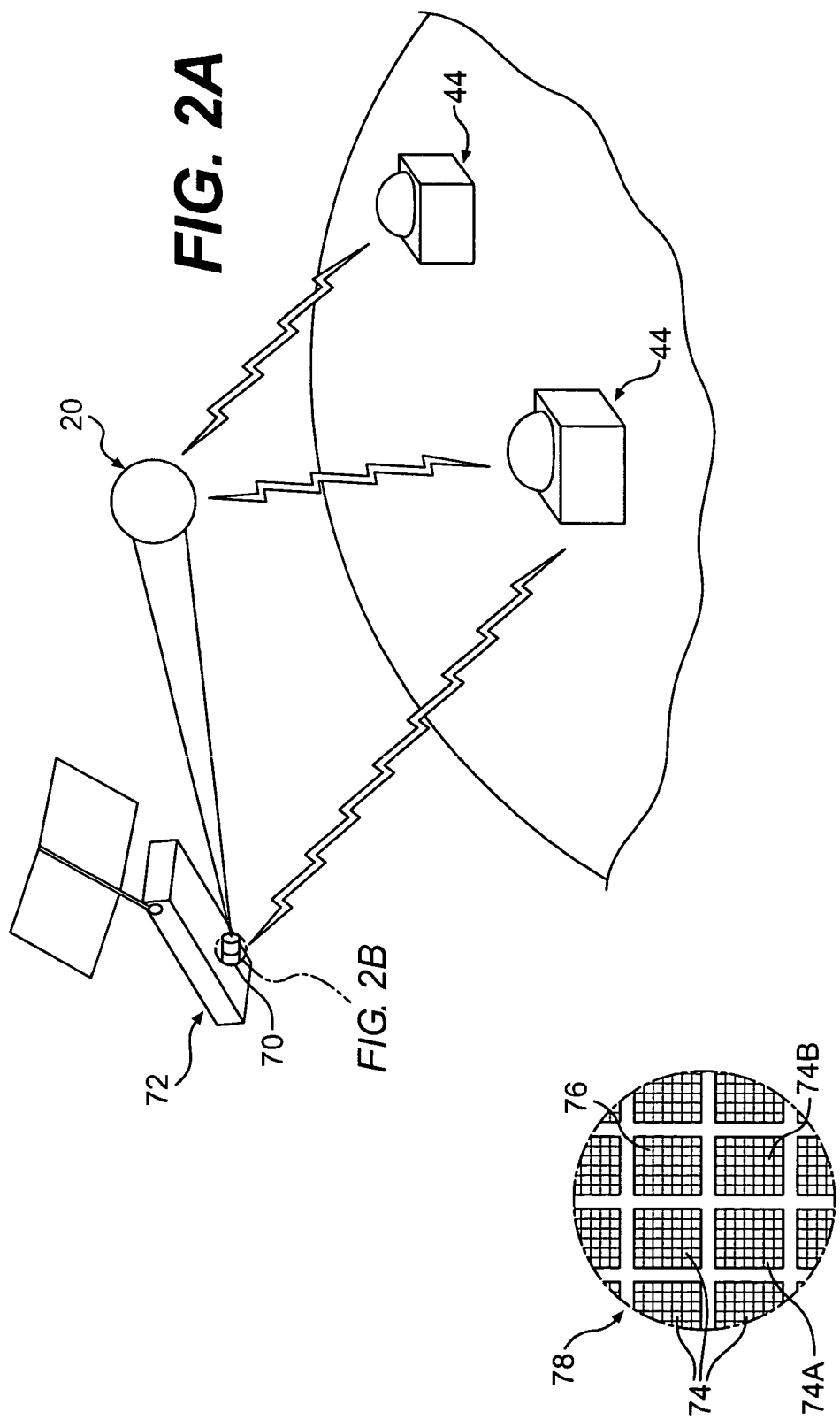
FIG. 2A is a schematic view of a system utilizing the device of FIG. 1.
FIG. 2B is a schematic detail view of a focal plane of a typical infrared sensor.

The device 20 further comprises a plurality of locator elements 42 disposed on the body 22, as shown in FIG. 1. The locator elements 42 allow the orbital position (i.e., ephemeris) of the device 20 to be accurately determined from a remote location (e.g., a ground station), while minimizing the disturbance to the radiant energy emitted by the device 20, irrespective of the viewing angle. In one embodiment, the locator elements 42 comprise optical-quality quartz corner reflectors for laser tracking. For example, two or three corner reflectors may be symmetrically mounted flush with the outer surface 28 of the shell 30 in one of the polar regions 36B. The relatively small reflectors allow the device 20 to be accurately tracked using a laser based at a ground station 44, as shown in FIG. 2A, while at the same time minimizing the variation in the radiant intensity of the body, as observed at a remote location, due to the location elements.

The device 20 further comprises a plurality of temperature sensors 46 disposed on the shell 30 to measure the temperature of the shell 30 proximate to the outer surface 28. An arrangement of 10 to 12 temperature sensors 46 has been found to provide an accurate characterization of the temperature distribution on the outer surface 28 of the shell 30. In one embodiment, 12 temperature sensors 46 are arranged in the plane containing the spin axis 24, and four temperature sensors 46 are located out-of-plane for crosscheck purposes. If a larger device is used and/or if greater accuracy in the measurement is required, additional temperature sensors 46 may be desirable. The temperature sensors 46 may also be used to verify on-orbit changes if any, occurring in the absorptivity and emissivity of the surface coatings.

The temperature sensors 46 may be expected to measure temperatures ranging from −150° C. to +150° C. and have an absolute accuracy and stability consistent with the requirements for determining the radiant intensity of the energy emitted from the device 20.

Figure 3:
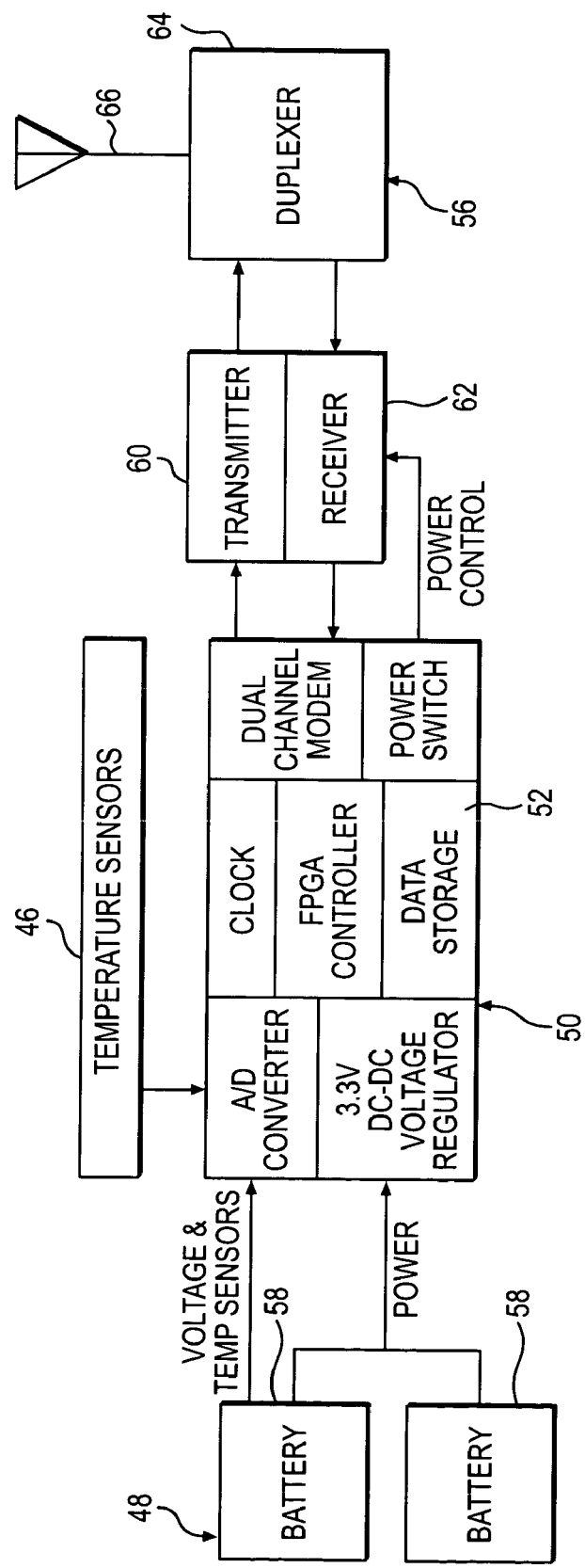
FIG. 3 is block diagram of an embodiment of the electronics of the device of FIG. 1.

The internal components of the device 20 comprise a power supply 48, control electronics 50, including an electronic data storage device 52, communications electronics 54, and an antenna system 56. The operational software associated with the system resides in the electronics of the device 20. These components are mounted on the platform 34 in the inner compartment 32 of the shell 30, as shown in FIG. 1. The internal components are shown schematically in FIG. 3. These components are selected such that their contribution to the external temperature of the body, and hence the radiant intensity of the body, is minimized.

The power supply 48 may include one or more batteries 58. The batteries 58 may be chosen from zinc-carbon, alkaline, mercury, zinc-silver oxide, zinc-air, lithium, lithium-oxyhalide, lithium-sulfur dioxide, lithium-thionyl chloride, lithium-oxychloride, lithium-manganese dioxide, and lithium-carbon monoflouride. Lithium power sources, in particular, provide a high energy density, have proven reliability, long life, energy capacity, and the ability to operate over a wide temperature range.

As shown in FIG. 1, two batteries 58 are mounted on the platform 34 on opposite sides of the body 22. In one embodiment, each battery 58 includes a plurality of lithium-oxyhalide cells having an open circuit voltage of approximately 35 volts, a load voltage of approximately 27 volts, and a stored energy of approximately 1600 watt-hours. Other arrangements of batteries may also be used.

The power supply 48 is operative for a finite lifetime, after which the device 20 operates passively, as explained below.

The control electronics 50 may include a Floating Point Gate Array (FPGA) controller, an electronic data storage device 52 having a random access memory (e.g., solid state and/or a mechanical disk), a dual channel modem (e.g., a modem for control and checkout of the system prior to launch), a power switch, a voltage regulator, an analog-to-digital signal converter, and a real-time clock.

The communications electronics 54 include a transmitter 60 and a receiver 62. In one embodiment, the transmitter 60 is an S-band fixed-frequency transmitter, which is capable of operating with a downlink frequency of 2230 MHz and of transmitting at data rates of 9600 bps or greater. The receiver 62 is an L-band receiver, which includes an FM modulator and a built-in bit synchronizer and is capable of receiving at data rates from 9600 bps to 10 Mbps. Both the transmitter 60 and the receiver 62 are designed to operate in the environments typically encountered in low earth orbit.

The antenna system 56 includes a duplexer 64 and an antenna 66 for transmitting data and for receiving commands from an external signal source (e.g., a ground station). In one embodiment, the antenna 66 is a short one-quarter wave monopole antenna having a length of approximately five centimeters. Such an antenna 66 may be formed of thin piano wire, in order to minimize external disturbances to the infrared signature of the device 20. The antenna 66 may be substantially coaxial with the spin axis of the body to minimize the variation in infrared intensity versus viewing angle of the body caused by the antenna 66.

The same monopole antenna may be used for both the transmitter's downlink and the receiver's uplink. In one embodiment, a monopole antenna having a peak gain of −2 dBi associated with the L-Band transmitter's uplink radiation pattern and a peak gain of +3 dBi associated with the S-Band receiver's downlink radiation pattern is used. The antenna 66 may extend from the shell 30 in the polar region 36B that provides the best transmission to and reception from the external signal source. The infrared profile of the external portion of antenna 66 is minimized in order to have a nominal effect on the overall infrared signature of the device 20.

During the lifetime of the power supply 48, the device 20 may be used to actively collect and transmit data to a ground station 44. The plurality of temperature sensors 46 collect temperature data at periodic intervals, such as, for example, 10-second intervals. At each data collection interval, the data from each temperature sensor 46 is acquired and stored in the memory of the data storage device 52. The temperature data is nominally associated with the time of collection, i.e., time tagged, when it is stored.

In another embodiment, the data may be collected only from those temperature sensors 46 for which the measured value is different from the preceding measurement. This may allow conservation of memory in the data storage device 52.

The stored data is transmitted to the ground station 44 periodically, for example, every seven to ten days, in short duration transmissions upon command from the ground station 44 or other remote source, as shown in FIG. 2A. Multiple ground stations 44 may be utilized in a network to communicate with the device 20. The data transmissions allow all of the stored data to be transmitted during a single pass of the device 20 over the ground station 44. In one example, where 560 kilobytes of data are transmitted at 9600 bps, the duration for transmitting the stored data is approximately eight minutes.

The device 20 further includes a photodiode detector 68, or other similar sensor, for receiving a signal from a ground station 44 or other external signal source. The photodiode detector 68 may be used as a backup device for receiving commands from the external signal source. For example, if the receiver 62 malfunctioned and was not able to receive commands, the photodiode detector 68 could be activated with a laser beam to trigger the transmitter 60 to turn on and/or transmit data.

The temperature data transmitted to the ground station 44 may be used to develop a thermal model of the body 22. The thermal model enables the calculation of the radiant intensity of the calibration verification device 20 over the course of its orbit, based on its known physical characteristics, including, for example, its diameter, its rate of spin, and the emissivity and absorptivity of its coating. Using the thermal model, the device's radiant intensity may be calculated for its entire orbital lifetime, including that period of time after which the batteries have lost all their charge and the electronics are thus non-operating. In addition, tracking the device 20 using the locator elements 42 provides accurate knowledge of the of the body's ephemeris even after the electronics within the body are non-operative.

The combined temperature and ephemeris data collected over the lifetime of the power supply 48 may also be used to verify, refine, and/or calibrate the thermal model used to predict the radiant intensity of a particular calibration verification device 20. Thus, an accurate understanding of the radiant intensity characteristics of the device 20 may be developed during the lifetime of the power supply 48, for example, during the first year on orbit. This understanding may be used to accurately predict the radiant intensity characteristics of the device 20 over its entire orbit lifetime, which may extend to 20 years or more, for example.

It is desirable to minimize the power consumption of the device 20 during the data collection and transmission period. Minimizing the power consumption extends the life of a given power supply 48 or allows the use of a smaller and lighter power supply 48. Further, minimizing the power consumption minimizes heat generation and reduces the likelihood that internal heat sources will significantly affect the infrared signature of the device 20. It is noted that after the data collection and transmission period ends and/or when the lifetime of the power supply 48 has been exceeded, there no longer exists any internal source of heat that could affect the infrared signature of the device 20.

The internal components of the device 20 may be operated in particular ways to minimize the power consumption. Several techniques include operating the internal components in a standby or sleep mode; collecting data periodically rather than continuously; turning on the receiver 62 only periodically, such as, for example, once every 100 seconds and/or only when the device 20 is within range of a ground station 44; and turning on the transmitter 60 when triggered by a ground command and downloading the stored data all at once, e.g., pulse burst transmission. Other operational techniques to reduce power consumption may also be used.

During the entire orbital lifetime of the device 20, its ephemeris, approximate temperature, and approximate radiant intensity are known at all times. The ephemeris may be accurately measured throughout the device's orbital lifetime by tracking the device using the locator elements 42.

Further, as described above, the temperature data is acquired and transmitted to a ground station 44 while the power supply 48 is operative. Based on the measured temperature data, a mathematical thermal model of the device 20 may be generated that allows the radiant intensity of the device 20 at the infrared frequency bands of interest to be predicted. The thermal model may be refined by comparing the predicted radiant intensity of the device 20 with the radiant intensity measured by an infrared sensor 70 based on a satellite 72, shown in FIG. 2A.

The refined thermal model may be used to predict the temperature and the radiant intensity of the device 20 when the power supply 48 is no longer operative. Thus, the device 20 may allow operators of satellites having infrared sensors to verify the calibration of the sensors located on satellites on a regular, or at-will, basis. This ability improves the accuracy of the measurements obtained from the sensors and also allows potentially multiple operators of the satellite systems to verify the operational capabilities of their systems, in real time, without requiring any active participation with the on-orbit portion of the calibration verification system, or with each other, for the entire orbital lifetime of the calibration verification system.

The device 20 may be used to assist in the calibration of infrared sensors by providing a known, invariant radiant intensity characteristic. An infrared sensor may then compare the detected radiant intensity of satellite to the known radiant intensity to verify the sensor's calibration.

In one example, the device's ephemeris is communicated by a ground station 44 to the control system of a satellite 72 containing the infrared sensor 70. The infrared sensor 70 is then commanded to view the region of space where the device 20 is located. In the case of a staring infrared array, the infrared sensor 70 is pointed in the direction where the device 20 is predicted to be entering into the sensor's field of view. The sensor 70 is then held fixed in that direction to view the device 20.

As the device 20 traverses the field of view of the infrared sensor 70, the radiant energy readings from the infrared sensor 70 are compared to the readings expected to be observed based on the distance from the device 20 to the sensor 70 and the predicted surface temperature of the device 20. This comparison may take place either on-board the satellite 72 or on the ground in a post-processing sense.

If the readings are consistent, the sensor 70 and its calibration are considered to be acceptable. If the measurements do not agree within a specified amount with the predicted measurements, then the calibration coefficients associated with the sensor 70 may be updated or a malfunction of the sensor 70 may be declared.

With the system of the present invention, multiple sensors, such as telescopes, for example, may use any calibration verification device 20 at any time to test their operation.

The device 20 is always available for verifying the calibration of an infrared sensor capable of viewing it. The device 20 may be used to verify calibration coefficients used with a plurality of pixels associated with an infrared sensor at various known energy levels. The device 20 may also be used to verify a calibration of an infrared sensor at various observed energy levels. Still further, the device may be used to verify a resolution capability of an infrared sensor.

Verifying the calibration coefficients used with a plurality of pixels allows an operator to verify the calibration of different groups 74 of pixels 76 on the sensor's focal plane 78, shown in FIG. 2B. For example, as the device 20 moves in orbit with respect to the satellite 72 containing the infrared sensor 70, the device's energy moves across the focal plane 78 of the infrared sensor 70.

The infrared radiant intensity of the outer surface 28 of the device 20 is measured using a first group 74A of one or more pixels 76 within the focal plane 78 to obtain a first measurement. The measurement is then repeated using a second group 74B of one or more pixels 76 to obtain a second measurement. The pixel-to-pixel calibration may be verified by comparing the value of the first measurement with the value of the second measurement. Further, the value of the first and second measurements may be compared with a predicted radiant intensity value.

FIG. 2B illustrates the focal array of a staring-type infrared sensor. Other types of infrared sensors, including scanning sensors utilizing a linear focal array, may also be used.

Verifying a calibration of an infrared sensor 70 at various observed energy levels allows an operator to assess the performance of the sensor 70 over a range of energy levels. The infrared radiant intensity of the outer surface 28 of the device 20 is measured using the infrared sensor 70 when the body 22 and the infrared sensor 70 are in a first geometrical relationship to obtain a first measurement. Next, the measurement is repeated when the body 22 and the infrared sensor 70 are in a second geometrical relationship to obtain a second measurement.

In the first geometrical relationship, the body 22 and the infrared sensor 70 are spaced at a first distance, and in the second geometrical relationship the body and the infrared sensor are spaced at a second distance greater than the first distance. Thus, the first measurement is carried out at a higher energy level.

The value of the first measurement may be compared with the value of the second measurement. Further, the value of the first measurement and the second measurement may be compared with a predicted radiant intensity value.

The calibration verification of the infrared sensor at various observed energy levels may be repeated at different energy levels corresponding to different distances between the sensor 70 and the device 20.

Verifying a resolution capability of an infrared sensor 70 allows an operator to assess the ability of the sensor 70 to distinguish among closely spaced objects. In this case, a plurality of devices 20 are deployed so as to be placed in orbit proximate to each other. The infrared radiant intensity of the outer surface 28 of each body 22 is measured using the infrared sensor 70. The sensor 70 may differentiate between the bodies 22 based on the infrared radiant intensity measurement.

Further, the sensor 70 may determine a respective location for each body 22 based on the infrared radiant intensity measurement. The respective locations may then be compared with an independently measured location for each body 22.

The above calibration verifications may also be combined. For example, the verification of the pixel-to-pixel calibration or the resolution calibration may be carried out at varying energy levels to simultaneously verify the linearity calibration of the sensor.

It will be apparent to those skilled in the art that various modifications and variations can be made to the structure and methodology described herein. Thus, it should be understood that the invention is not limited to the examples discussed in the specification. Rather, the present invention is intended to cover modifications and variations.

What is claimed is:

1. A device for verifying the calibration of an infrared sensor, comprising:
   a body configured to be placed in orbit, the body comprising a shell, an outer surface, and a spin axis, wherein the shell comprises a first thickness proximate a polar region and a second thickness, proximate an equator region, that is different than the first thickness, and wherein the outer surface has an infrared radiant intensity that is substantially independent of a viewing angle between the spin axis and the infrared sensor.

2. The device of claim 1, further comprising at least one reflector element disposed on the body.

3. The device of claim 2, wherein the at least one reflector element comprises a plurality of locator elements.

4. The device of claim 2, wherein the at least one reflector element comprises a reflector for a laser.

5. The device of claim 2, further comprising:
   at least one sensor associated with the body; and
   a power supply.

6. The device of claim 5, further comprising a transmitter for transmitting data obtained by the at least one sensor.

7. The device of claim 6, further comprising a data storage device for storing data obtained by the at least one sensor.

8. The device of claim 7, wherein the transmitter transmits data from the data storage device.

9. The device of claim 6, further comprising a receiver for receiving control signals.

10. The device of claim 9, wherein the transmitter transmits data in response to a control signal received by the receiver.

11. The device of claim 9, further comprising a monopole antenna utilized by the transmitter in transmitting data and by the receiver in receiving data.

12. The device of claim 9, wherein the outer surface has an infrared radiant intensity that is substantially independent of operation of the transmitter and the receiver.

13. The device of claim 5, wherein the at least one sensor comprises a temperature sensor.

14. The device of claim 13, wherein the at least one sensor comprises a plurality of temperature sensors.

15. The device of claim 5, wherein the power supply comprises at least one of a lithium battery, a lithium oxyhalide battery, a lithium-sulfur dioxide battery, a lithium-thionyl chloride battery, a lithium-oxychloride battery, a lithium-manganese dioxide battery, a lithium-carbon monoflouride battery, a zinc-carbon battery, an alkaline battery, a mercury battery, a zinc-silver oxide battery, and a zinc-air battery.

16. The device of claim 1, wherein the body has a substantially spherical shape.

17. The device of claim 1, wherein the shell defines an inner compartment.

18. The device of claim 1, wherein the shell comprises at least one of aluminum, titanium, steel, copper, nickel, magnesium, fiberglass, a graphite composite, and a Kevlar-reinforced epoxy.

19. The device of claim 1, wherein the spin axis is associated with a first principal moment of rotational inertia at a first rotational frequency, the spin axis being oriented such that thermal stability of the body can be maintained by keeping radiation from the sun at a known angle with respect to the spin axis of the body.

20. The device of claim 19, wherein the spin axis is substantially perpendicular to an ecliptic plane of the body.

21. The device of claim 1, wherein the outer surface has an emissivity ranging from approximately 0.1 to approximately 1.0 over a radiant energy range of interest.

22. The device of claim 1, wherein the outer surface has an infrared radiant intensity ranging from approximately $10^{-1}$ Watts per steradian to approximately 10 Watts per steradian.

23. A device for verifying the calibration of an infrared sensor, comprising:
    a body configured to be placed in orbit, the body comprising a shell, an outer surface, and a spin axis, wherein the shell comprises a mass girdle disposed proximate an ecliptic plane and formed from a plurality of plates secured to an inner surface of the shell, and wherein the outer surface has an infrared radiant intensity that is substantially independent of any internal heat sources;
    at least one thermal sensor disposed on the body;
    a transmitter for transmitting data obtained by the at least one thermal sensor;
    a receiver for receiving control signals, wherein the transmitter transmits data in response to a control signal received by the receiver;
    a power supply; and
    at least one locator element disposed on the body, wherein the at least one locator element is configured to allow the device to be tracked by an external tracking device.

24. The device of claim 23, wherein the outer surface has an infrared radiant intensity that is substantially independent of a viewing angle between the spin axis and the infrared sensor.

25. The device of claim 23, wherein the shell is substantially spherical and defines an inner compartment.

26. The device of claim 23, further comprising a data storage device for storing data obtained by the at least one thermal sensor, wherein the transmitter transmits data from the data storage device.

27. The device of claim 23, wherein the at least one locator element comprises a plurality of reflectors for a laser.

28. The device of claim 23, further comprising a monopole antenna utilized by the transmitter in transmitting data and by the receiver in receiving data.

29. A method of verifying calibration coefficients used with a plurality of pixels associated with an infrared sensor at various known energy levels, comprising:
    providing a body comprising a shell, an outer surface, and a spin axis, wherein the shell comprises a first thickness proximate a polar region and a second thickness, proximate an equator region, that is different than the first thickness, and wherein the outer surface has an infrared radiant intensity that is substantially independent of a viewing angle between the spin axis and the infrared sensor;
    placing the body in orbit;
    measuring the infrared radiant intensity of the outer surface using a first group of one or more pixels associated with the infrared sensor to obtain a first measurement; and
    measuring the infrared radiant intensity of the outer surface using a second group of one or more pixels associated with the infrared sensor to obtain a second measurement.

30. The method of claim 29, further comprising determining an orbital position of the body using at least one locator element disposed on the body.

31. The method of claim 29, further comprising comparing the value of the first measurement with the value of the second measurement.

32. The method of claim 29, further comprising:
    comparing the value of the first measurement with a predicted radiant intensity value; and
    comparing the value of the second measurement with the predicted radiant intensity value.

33. A method of verifying a resolution capability of an infrared sensor, comprising:
    providing a plurality of bodies, each body comprising a shell, an outer surface, and a spin axis, wherein the shell comprises a first thickness proximate a polar region and a second thickness, proximate an equator region, that is different than the first thickness, and wherein the outer surface has an infrared radiant intensity that is substantially independent of a viewing angle between the spin axis and the infrared sensor;
    placing the bodies in orbit proximate to each other; and
    measuring the infrared radiant intensity of the outer surface of each body using the infrared sensor.

34. The method of claim 33, further comprising determining an orbital position of each body using at least one reflector element disposed on each body.

35. The method of claim 33, further comprising differentiating between the bodies based on the infrared radiant intensity measurement.

36. The method of claim 33, further comprising determining a respective location for each body based on the infrared radiant intensity measurement.

37. The method of claim 36, further comprising comparing the respective location for each body with an independently measured location for each body.

38. The device of claim 1, wherein the second thickness is greater than the first thickness.

39. The device of claim 1, wherein at least one of the first and second thicknesses are not constant.

40. The device of claim 1, wherein at least one of the first and second thicknesses assists in equalizing a temperature distribution experienced by the shell.

41. The device of claim 23, wherein the mass girdle assists in establishing a first moment of inertia around the spin axis.

42. The device of claim 23, wherein the mass girdle is formed from a different material than the shell.

* * * * *